United States Patent [19]

Hider et al.

[11] Patent Number: 5,185,319

[45] Date of Patent: Feb. 9, 1993

[54] STABILIZATION OF ORGANIC COMPOUNDS

[75] Inventors: Robert C. Hider, Clacton; Michael A. Stockham, Saffron Waldon, both of England

[73] Assignee: National Research Development Corporation, London, England

[21] Appl. No.: 520,203

[22] Filed: May 3, 1990

[30] Foreign Application Priority Data

May 8, 1989 [GB] United Kingdom ............... 8910521

[51] Int. Cl.$^5$ .................. A61K 37/26; C07K 5/00
[52] U.S. Cl. ....................................... 514/3; 514/866; 530/303; 546/261; 546/290; 546/298
[58] Field of Search ............ 514/3, 866; 546/261, 546/290, 298; 530/303

[56] References Cited

U.S. PATENT DOCUMENTS 4,698,431 10/1987 Raymond et al. .
4,783,441 11/1988 Thurow ................................ 514/3

FOREIGN PATENT DOCUMENTS 93498 3/1983 European Pat. Off. .
120669 10/1984 European Pat. Off. .
138420 4/1985 European Pat. Off. .
138421 4/1985 European Pat. Off. .
58-22200 12/1983 Japan .
58-222007 12/1983 Japan .
59-00710 1/1984 Japan .

OTHER PUBLICATIONS

Reynolds (ed), Martindale, 29th Ed. 1989 pp. 1355-1359.
CA vol. 100 (1984) No. 144827f of Devra Japan 59007108.
Kontoghiorghes et al. Arzneim-ForschDrug Res. 37(11) Nr. 11 (1987) 1099-1102.
Kim et al., "2-Pyridon-1-yl Diphenyl Phosphate ... ", Journal of the Chemical Society, Chemical Communications, 1986, No. 9, p. 719.
Horiki et al., "Neighbouring Group Participation in Peptide Synthesis . . . ", Heterocycles, 1978, 10, pp. 185-198.
Windholz (ed), "Butylated Hydroxyanisole . . . ", The Merck Index, 10th edition, 1983, Merck & Co. Inc., Ratway, pp. 1521-1522 & 7764.
Hider et al., "The Effect of Insulin on Free . . . ", Biochem. J., 125, 751-756, (1971).

Primary Examiner—Jeffrey E. Russel
Assistant Examiner—B. Celsa
Attorney, Agent, or Firm—Nixon & Vanderhye

[57] ABSTRACT

Admixture of insulin and a hydroxypyridone being: (1) a 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or more substituents selected from aliphatic acyl, alkoxy, cycloalkoxy, aliphatic amide, aliphatic ester, halogen and hydroxy groups and, optionally, in which one or more of the hydrogen atoms attached to ring carbon atoms are replaced by an aliphatic acyl, alkoxy, cycloalkoxy, aliphatic amide, aliphatic ester, halogen or hydroxy group, by an aliphatic hydrocarbon group, or by an aliphatic hydrocarbon group substituted by an alkoxy, cycloalkoxy, aliphatic ester, halogen or hydroxy group, or a salt thereof.

13 Claims, 1 Drawing Sheet

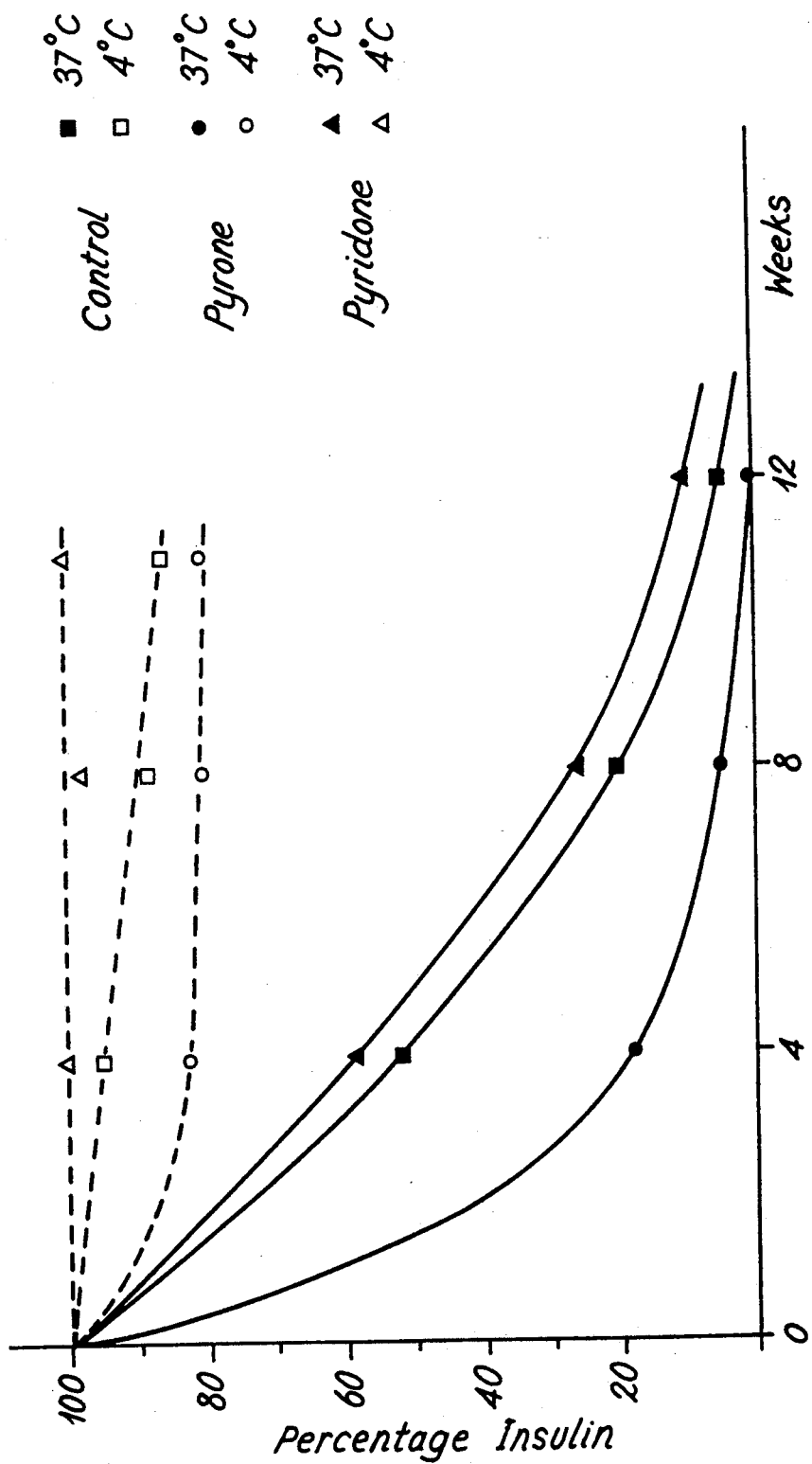

STABILIZATION OF ORGANIC COMPOUNDS

This invention relates to the stabilization of organic compounds, in particular of peptides and proteins.

BACKGROUND OF THE INVENTION

Peptides and proteins can show instability with cleavage occurring at

bonds therein to form smaller molecules. Different theories have been advanced as to which amino acid residues are particularly likely to lead to instability, one of these identifying histidine and proline residues. Considerable problems can arise in the manufacture and storage of such compounds as a consequence of their lack of stability which can be illustrated by reference to one of the commonest of the various peptides and proteins used in therapy, insulin, which is used for the treatment of diabetes mellitus. Thus insulin can form aggregates and, although this is not of itself disadvantageous, if these undergo chemical modification so that they will not disaggregate in vivo this will have the effect of lowering the physiological activity of the insulin. Moreover, chemical modification of insulin may result in a product which is recognized by the immune system as foreign with the possibility of the development of an allergic reaction by the patient.

We have investigated a variety of chelating agents to see whether they are suitable to effect stabilization of peptide and protein materials used for therapeutic or other purposes. Surprisingly, we have found for example that whilst certain chelating agents such as ethylene diamine tetra-acetic acid and 3-hydroxy-2-methyl-4-pyrone have no stabilizing effect on insulin, and indeed can exhibit a destabilizing effect, certain other chelating agents do effect stabilization, particularly at about 4° C. Such stabilization at a low temperature is of considerable importance since insulin is stored in solution form or in the freeze dried state at about 4° C. prior to use or at about −10° C. during various stages of manufacture and shipment of the bulk product.

DESCRIPTION OF THE INVENTION

Accordingly the present invention comprises a mixture of a peptide or protein and a hydroxypyridone being:

(1) a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or more substituents selected from aliphatic acyl, alkoxy, cycloalkoxy, aliphatic amide, aliphatic ester, halogen and hydroxy groups and, optionally, in which one or more of the hydrogen atoms attached to ring carbon atoms are replaced by an aliphatic acyl, alkoxy, cycloalkoxy, aliphatic amide, aliphatic ester, halogen or hydroxy group, by an aliphatic hydrocarbon group, or by an aliphatic hydrocarbon group substituted by an alkoxy, cycloalkoxy, aliphatic ester, halogen or hydroxy group, or a salt thereof;

(2) a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy and cycloalkoxy groups and alkoxy and cycloalkoxy groups substituted by an alkoxy, cycloalkoxy, aliphatic amide, aliphatic eter, halogen or hydroxy group, and aliphatic hydrocarbon groups and aliphatic hydrocarbon groups substituted by an alkoxy, cycloalkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group, or a salt thereof; or (3) a compound in which two or more rings, being selected from 3-hydroxypyrid-2-ones, 3-hydroxypyrid-4-ones and 1-hydroxypyrid-2-ones, are covalently linked with the rings retaining their adjacent hydroxy and oxo groups; but excluding any occurrence of the mixture in vivo.

The invention may be applied to the stabilization of the carbon-nitrogen bond of groupings

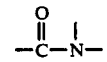

in various peptides and proteins, particularly those having a biological activity of one form or another including animal and plant hormones, for example parathyroid hormone, calcitonin, corticotrophin, cytokines, growth hormones and particularly insulin, hormones controlling the release of other compounds, which compounds are often themselves hormones, for example gonadotrophin releasing hormone, LHRH and LHRH antagonists, immunoglobulins, for example monoclonal antibodies, blood coagulation factors, for example Factor VIII, enzymes and enzyme inhibitors, for example thrombin, as well as fragments of each of these. The term insulin is used herein to include not only the naturally occurring hormone of various species, for example human, bovine and porcine insulin, but also synthetic versions of the natural hormone and synthetic analogues thereof possessing the hormone activity.

In addition to the stabilization of insulins, other areas of peptide and protein stabilization in which the present invention is particularly applicable include vaccines, i.e. products comprising antigenic materials or antibodies, anti-allergy products in general and particularly the various forms of blood products. Such blood products include human plasma, fibrinogen, immunoglobulins, blood coagulation factors such as Factor VIII, and thrombin and suffer from similar storage problems to those experienced with the insulins.

Conveniently, the invention may be used with hexapeptides and higher peptides or proteins, more especially with decapeptides, and particularly eicosapeptides, and higher peptides or proteins. In molecular weight terms the preference is for the use of a peptide or protein with a molecular weight of 500 or 600 daltons or more, for example 1,200 or 2,400 daltons or more. Thus, the instability of peptides and proteins is most pronounced where the chain is long enough to undergo folding with consequent interactions between different parts of it, although certain amino acids such as methionine can induce instability even without such folding of the peptide or protein occurring.

The materials stabilized may of course contain other groupings than linked amino acid residues, for example glycosyl groups, or may contain other compounds mixed with the peptides and proteins.

Hydroxypyridone compounds of types (1), (2) and (3) are described in detail in UK patents GB 2118176B and 2136807B; GB 2146990B; and GB 2146989B, respectively, which relate to the use of such compounds for the removal of toxic amounts of metal from the body, and the various preferred and specific types of compound described in these patents may be used in the present invention. Certain compounds of types (2) and (3) are also described in U.S. Pat. No. 4,698,431.

Among the compounds of these earlier patents which may be mentioned particularly are those in which the rings are unsubstituted apart from linking groups in the case of those compounds containing two or more rings, and, for both these compounds and the single ring compounds, those in which the rings are substituted by aliphatic hydrocarbon groups (in the case of the 3-hydroxypyridones and particularly on the nitrogen atom of the ring), by aliphatic hydrocarbon groups substituted by a hydroxy or cycloalkoxy or particularly an alkoxy group or by more than one, for example two of such groups (in the case of the 1- and 3-hydroxypyridones and particularly on the nitrogen atom of the ring in the latter case), or by an aliphatic amide group or an alkoxy or cycloalkoxy group substituted by an alkoxy, cycloalkoxy, aliphatic amide or hydroxy group (in the case of the 1-hydroxypyridones). The size of the aliphatic hydrocarbon and alkyl or cycloalkyl moieties in such groups (including those in the aliphati amide groups) is conveniently in a range of $C_{1-8}$, particularly $C_{1-6}$, for example $C_{1-4}$, such as methyl and ethyl.

The hydroxypyridones of use in the present invention are discussed in detail in the earlier patents but compounds of particular interest in the context of the present invention are water soluble, neutral compounds of a hydrophilic character. As explained in these earlier patents it is possible to balance the presence of a hydrophilic substituent by the presence of one or more hydrophobic substituents but in order to achieve the appropriate hydrophilic character in the compound it is preferred, for example, that the number of carbon atoms in the aliphatic hydrocarbon, alkoxy and cycloalkoxy moieties and such substituted moieties is limited. Thus the aliphatic hydrocarbon groups are conveniently of 1 to 4 carbon atoms, especially 1 or 2 carbon atoms, when these groups are not themselves substituted. Acyclic rather than cyclic groups are preferred, as are saturated rather than unsaturated groups, the preferred unsubstituted aliphatic hydrocarbon groups and those in the aliphatic amide groups being the alkyl groups ethyl and particularly methyl. The substituted aliphatic hydrocarbon groups are conveniently of 1 to 6 carbon atoms, preferably of 1 to 4 carbon atoms, especially of 1, 2 or 3 carbon atoms. Once again acyclic rather than cyclic, and saturated rather than unsaturated groups are preferred, the preferred substituted aliphatic hydrocarbon groups being substituted methyl, ethyl, isopropyl and n-propyl groups, the three latter alkyl groups conveniently being substituted terminally. Alkoxy groups are preferred to cycloalkoxy groups and the former are conveniently of 1 to 6 carbon atoms, preferably of 1 to 4 carbon atoms and especially of 1 or 2 carbon atoms. Aliphatic amide groups conveniently contain no more than one aliphatic hydrocarbon group which may, for example, be ethyl or especially methyl.

Specific examples of substituted aliphatic hydrocarbon group substituents are hydroxymethyl, 2-hydroxyethyl, 3-hydroxypropyl, methoxymethyl, 2-methoxyethyl, 3-methoxypropyl, 2-methoxy-1-methylethyl, ethoxymethyl, 2-ethoxyethyl, 3-ethoxypropyl, and 2-ethoxy-1-methylethyl, the groups in which the oxygen atom is attached to the bonding carbon atom of the group being of less interest in the case of N-substituents in view of the lesser stability of the grouping

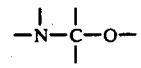

as compared with

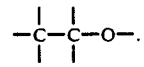

As regards both the single ring compounds and those containing two or more rings, among the 3-hydroxypyridones it is the 3-hydroxypyrid-4-ones which are of especial interest and there is also particular interest in the 1-hydroxypyrid-2-ones. Thus, a first preferred group of compounds consists of single ring 3-hydroxypyrid-4-ones in which the carbon atoms of the ring each separately are either unsubstituted or are substituted by an aliphatic hydrocarbon group, for example as described above, conveniently at the 6- or particularly at the 2-position, the nitrogen atom being substituted either by an aliphatic hydrocarbon group or by a hydroxy-substituted or particularly an alkoxy-substituted aliphatic hydrocarbon group, for example as described above. Specific examples of such compounds are 3-hydroxy-1,2-dimethylpyrid-4-one, 1-ethyl-3-hydroxy-2-methyl-pyrid-4-one, 3-hydroxy-1-(2'-hydroxyethyl)-2-methylpyrid-4-one, 3-hydroxy-1-(2'-hydroxy-1'-methylethyl)-2-methylpyrid-4-one, 3-hydroxy-1-(2'-hydroxypropyl)-2-methylpyrid-4-one, 3-hydroxy-1-(3'-hydroxypropyl)-2-methylpyrid-4-one, 3-hydroxy-1-(2'-methoxyethyl)-2-methylpyrid-4-one, 3-hydroxy-1-(2'-methoxy-1'-methylethyl)-2-methylpyrid-4-one, 3-hydroxy-1-(2'-methoxypropyl)-2-methylpyrid-4-one, 3-hydroxy-1-(3'-methoxypropyl)-2-methylpyrid-4-one, 1-(2'-ethoxyethyl)-3-hydroxy-2-methylpyrid-4-one, 1-(2'-ethoxy-1'-methylethyl)-3-hydroxy-2-methylpyrid-4-one, 1-(2'-ethoxypropyl)-3-hydroxy-2-methylpyrid-4-one, 1-(3'-ethoxypropyl)-3-hydroxy-2-methylpyrid-4-one, and salts thereof. Other specific examples include analogues of the compounds just mentioned in which the methyl group at the 2-position is replaced by an ethyl group, for example 1,2-diethyl-3-hydroxypyrid-4-one, and salts thereof. Of especial interest are the compounds containing a methoxy group, particularly 3-hydroxy-1-(2'-methoxyethyl)-2-methylpyrid-4-one and salts thereof.

A second preferred group of compounds consists of single ring 1-hydroxypyrid-2-ones in which the carbon atoms of the ring are substituted, conveniently at the 6- or 4-position by an alkoxy, alkoxyalkoxy or aliphatic amide substituent. Specific examples of such compounds are 1-hydroxy-4-(2'-methoxyethoxy)-pyrid-2-one, 1-hydroxy-4-(2'-ethoxyethoxy)-pyrid-2-one, and 6-carbamoyl-1-hydroxypyrid-2-one and its 6-(N- methylcarbamoyl) and 6-(N-ethylcarbamoyl) analogues, and salts thereof.

A third preferred group of compounds consists of compounds containing three 3-hydroxypyrid-2- or 4-one rings in which the carbon and nitrogen atoms of the rings are either unsubstituted apart from linking groups or are substituted by an aliphatic hydrocarbon group, for example as described above, particularly at the 6-, or especially at the 2-position in the case of the 4-ones.

A fourth preferred group consists of compounds containing three 1-hydroxypyrid-2-one rings in which the carbon atoms of the rings are either unsubstituted apart from linking groups or are substituted by an aliphatic hydrocarbon group or an aliphatic amide group, for example as described above, particularly at the 6-or 4-position. Linkage of the rings through the carbon atoms thereof or particularly through the nitrogen atoms thereof for the 3-hydroxypyridones is conveniently effected by linking groups which are of an aliphatic hydrocarbon nature or which additionally contain one or more groups

Specific examples of such compounds are the compound N,N-di-[2-(3-hydroxy-2-oxopyrid-1-ylacetamido)-ethyl]-2-(3-hydroxy-2-oxopyrid-1-ylacetamido)-ethylamine of Example 8 of GB 2146989B (and compounds 6B, 6C, 9 and 10 listed in Table 4 of that patent.

Certain types of hydroxypyridone compound may be more suited than others for use in particular environments. Thus peptides and proteins may be stored at various pHs, different forms of insulin preparation in particular being stored at both acidic and alkaline pHs. For pHs in the range of about 3-5 the 1-hydroxypyrid-2-one compounds, either in single ring or multi-ring form, for example the three ring form, are of particular interest whilst for higher pHs the 3-hydroxypyrid-4-one compounds, either in single ring or multi-ring form, for example the three ring form, are of particular interest.

The hydroxypyridones may be prepared by procedures described in the four earlier patents referred to hereinbefore. In particular, the C-carbamoyl and -alkylated carbamoyl 1-hydroxypyridones may be prepared as described in U.S. Pat. No. 4,698,431 and the N-alkoxyalkyl and N-hydroxyalkyl 3-hydroxypyrid-4-one compounds may be prepared as described in UK patent GB 2136807B. This latter route involves reaction of a corresponding 3-hydroxy-4-pyrone, or a 3-hydroxy-4-pyrone containing groups convertible to the C-substituents present in the desired hydroxpyridone, with a compound R'NH$_2$ in which R' represents the group present on the nitrogen atom of the desired compound or a group convertible thereto, the reaction being carried out in the presence of a base, for example an alkali metal hydroxide such as sodium hydroxide. This procedure is specifically exemplified in GB 2136807B for 3-hydroxy-1-(2'-hydroxyethyl)-2-methylpyrid-4-one and compounds containing larger N-hydroxyalkyl groups, and may be applied in an exactly analogous fashion to the preparation of the corresponding N-alkoxyalkyl compounds. Thus the use of 2-methoxyethylamine in place of 2-hydroxyethylamine in Example 11 of GB 2136807B will yield the compound 3-hydroxy-1-(2'-methoxyethyl)-2-methylpyrid-4-one which is of some particular interest.

Where appropriate, the hydroxypyridones may be used in salt form, particularly as a physiologically acceptable salt. Thus salts may be formed between the anion produced by the loss of the hydroxy group proton and a cation such as an alkali metal ion, for example Na$^+$, quaternary ammonium ions or protonated amines such as tris (tris represents 2-amino-2-hydroxymethyl propane 1,3-diol). As an alternative to salt formation with a base, the nitrogen atom of a 3-hydroxypyridone ring may be sufficiently basic, particularly in the case of the 3-hydroxypyrid-4-ones, for salt formation to be effected through reaction with an acid such as hydrochloric acid. It will be appreciated that when the peptide or protein is in solution the question of whether it is appropriate to use a salt will depend on the pH of the solution, salts formed with a cation being appropriate for use at above about pH 5 in the case of the 1-hydroxypyridones and above about pH 9 in the case of the 3-hydroxypyrid-4-ones, whilst the 3-hydroxypyrid-4-one salts formed with an anion are appropriate for use at above about pH 7.

The present invention is particularly applicable to the stabilization of peptides and proteins at ambient temperatures or below, for example down to $-10°$ C., especially at 10° C. or less and particularly at 4° C. or less, although it is also of interest for use at about 37° C., especially when using compounds incorporating more than one hydroxypyridone ring, for example the hexadentate three ring compounds.

The proportion of hydroxypyridone compound to peptide or protein may vary depending on the nature of the individual materials involved and the conditions to which the stabilized peptide or protein is subjected. However, by way of guidance it may be stated that the use of a ratio by weight of the hydroxypyridone: the peptide or protein of from 0.01:1 to 100:1, particularly from 0.1:1 to 10:1, for example 2:1, is often suitable.

Where desired more than one hydroxypyridone compound may be used, for example both a single ring bidentate compound and a three ring hexadentate compound, the proportions given then applying to the total of hydroxypyridone compounds.

As indicated, on occasion the mixture may consist only of the hydroxypyridone(s) and the peptide or protein but in many other instances the mixture may contain other ingredients, for example diluents particularly in the form of solvents such as water, etc., and/or compounds which further enhance the stability of the peptide or protein. A component of potential value in the latter category is zinc which may be provided in the form of various types of zinc-containing compound although these will often be required to be of a physiologically acceptable form and amount. Examples of suitable compounds are zinc salts such as zinc chloride, particularly when the peptide protein is in an environment of pH$\leq$5.0 and zinc hydroxypyridone complexes, particularly when the peptide or protein is in an environment of pH$\geq$5.0, such complexes conveniently being of a hydroxypyridone as described herein, for example of the same one as is present in metal-free form. Such complexes are further described in U.K. Patent GB 2148896 for the single ring 3-hydroxypyridone compounds and the zinc complexes of the single ring 1-hydroxypyridones and of the multi ring compounds may be prepared in a generally similar fashion. Conveniently an excess of hydroxypyridone to zinc is used, for example a molar ratio of at least four moles of hydroxypyridone ring to each mole of zinc.

Very often the mixture may be in the form of a pharmaceutical composition containing the peptide or protein and hydroxypyridone materials together with a physiologically acceptable diluent or carrier. The nature of such compositions may be of various forms, many of which are described in the five earlier patents in the context of the formulation of the hydroxypyridones as therapeutic agents. In the context of insulin, sterile and pyrogen-free aqueous solutions and suspensions for injection are of particular interest. These and other formulations of peptides and proteins to which the invention may be applied are described in the art in relation to the peptide or protein in question.

The hydroxypyridones are relatively non-toxic compounds and pharmaceutical compositions in which the active component is a peptide or protein stabilized by a hydroxypyridone in a proportion as indicated herein will usually be quite acceptable for direct use.

The present invention therefore further includes a pharmaceutical composition which comprises a mixture of a physiologically active peptide or protein and a hydroxypyridone being:

(1) a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or more substituents selected from aliphatic acyl, alkoxy, cycloalkoxy, aliphatic amide, aliphatic ester, halogen and hydroxy groups and, optionally, in which one or more of the hydrogen atoms attached to ring carbon atoms are replaced by an aliphatic acyl, alkoxy, cycloalkoxy, aliphatic amide, aliphatic ester, halogen or hydroxy group, by an aliphatic hydrocarbon group, or by an aliphatic hydrocarbon group substituted by an alkoxy, cycloalkoxy, aliphatic ester, halogen or hydroxy group, or a salt thereof;

(2) a 1-hydroxypyrid-2-one in which one or more of the hydrogen atoms attached to ring carbon atoms are replaced by a substituent selected from aliphatic acyl, aliphatic amide, cyano, aliphatic ester, halogen and hydroxy groups, alkoxy and cycloalkoxy groups and alkoxy and cycloalkoxy groups substituted by an alkoxy, cycloalkoxy, aliphatic amide, aliphatic eter, halogen or hydroxy group, and aliphatic hydrocarbon groups and aliphatic hydrocarbon groups substituted by an alkoxy, cycloalkoxy, aliphatic ester, halogen or hydroxy group, but excluding compounds in which said replacement of hydrogen atoms is effected only by substituents selected from aliphatic hydrocarbon groups, halogen groups and aliphatic hydrocarbon groups substituted by a halogen group, or a salt thereof; or (3) a compound in which two or more rings, being selected from 3-hydroxypyrid-2-ones, 3-hydroxypyrid-4-ones and 1-hydroxypyrid-2-ones, are covalently linked with the rings retaining their adjacent hydroxy and oxo groups, together with a physiologically acceptable diluent or carrier.

The composition will generally contain a therapeutically effective amount of the peptide or protein as indicated in the literature as being suitable to produce the desired physiological effect.

In producing the mixture the hydroxypyridone and peptide or protein components may be mixed in the solid form or in solution depending on the physical nature of the mixture to be stabilized, standard mixing procedures conveniently being applicable. Most usually, however, the final stabilized pharmaceutical composition containing a peptide or protein/hydroxypyridone mixture will be stored in solution form or, to a lesser extent, in freeze dried form. Thus, although it is quite common practice to produce freeze dried preparations of peptides and proteins because of the lack of stability of their solutions, the present invention may enable materials which are normally lyophilised to be produced in solution form owing to the stabilizing effect of the hydroxypyridone compounds.

In addition to their stabilizing effect the hydroxypyridones may exert another beneficial effect in some circumstances. Thus there is a potential problem with both synthetic and bioengineered peptides and proteins in that these may become contaminated with iron, nickel, zinc and aluminium from HPLC purification procedures. Such metals will bind preferentially to the hydroxypyridones rather than to the peptide or protein in which condition they are more acceptable when the contaminated peptide or protein is administered. It may be appropriate to increase the proportion of hydroxypyridone compound: peptide or protein if a significant amount of such contamination is anticipated.

BRIEF DESCRIPTION OF THE FIGURE

The invention will now be further described in the following examples with reference to the attached FIGURE which is a graph showing the percentage amount of insulin present in various incubated solutions after certain periods of time.

EXAMPLES

The invention is illustrated by the following examples:

EXAMPLE 1

Injectable Formulation of Insulin

A sterile pyrogen-free aqueous solution of pH 7.0 containing
- sodium bicarbonate (12 mM)
- sodium phosphate (54 mM)
- phenol (0.2% w/v)
- glycerol (1.6% w/v)
- insulin (bovine, porcine or human-10 units/ml; approximately $10^{-4}$M)
- 3-hydroxy-1-(2'-methoxyethyl)-2-methylpyrid-4-one (100 μM)

is prepared by dissolving the ingredients at the concentrations indicated in sterile and pyrogen-free water under aseptic conditions to provide an injectable preparation of insulin[1].

(1) Alternative forms of formulation of insulin may be of other standard types, for example prompt insulin zinc suspension, globin zinc insulin injection, isophane insulin suspension, insulin zinc suspension and protamine zinc insulin suspension, but additionally containing a similar amount of 3-hydroxy-1-(2'-methoxyethyl)-2-methypyrid-4-one.

EXAMPLE 2

Comparison of Stabilizing Effect of 3-hydroxy-1-(2'-methoxyethyl)-2-methylpyrid-4-one and 3-hydroxy-2-methyl-4-pyrone A solution was prepared corresponding to that described in Example 1 containing porcine insulin and being pyrogen-free but not sterile. For comparative purposes a further solution was prepared in which the hydroxypyridone was replaced by the alternative chelating agent 3-hydroxy-2-methyl-4-pyrone.

The solutions were incubated at either 4° C. or 37° C. and the stability of the insulin was studied over a period of 12 weeks through use of the reverse phase HPLC method described by Seipke et al, Angew. Chem. Int. Ed. Engl., 1986, 25, 535–552 and by Grau, Diabetologia, 1985, 28, 458–463. The amount of insulin present in the solution at 4, 8 and 12 weeks was then calculated as a percentage of the original amount present.

The results are shown in the Figure from which it will be seen that 3-hydroxy-2-methyl-4-pyrone destabilises insulin at both 37° C. and 4° C. whilst 3-hydroxy-1-(2'-methoxyethyl)-2-methylpyrid-4-one stabilises insulin, to some extent at 37° C., but particularly at 4° C. when no degradation was observed over the whole period of 12 weeks.

We claim:

1. A mixture of an insulin and a 3-hydroxypyrid-4-one in which the hydrogen atom attached to the nitrogen atom is substituted by an aliphatic acyl group, by an aliphatic hydrocarbon group, or by an aliphatic hydrocarbon group substituted by one or more substituents selected from the group consisting of aliphatic acyl, alkoxy, cycloalkoxy, aliphatic amide, aliphatic ester, halogen and hydroxy groups and in which the carbon atoms of the ring of the 3-hydroxypyrid-4-one each separately are either unsubstituted or substituted by an aliphatic acyl, alkoxy, cycloalkoxy, aliphatic amide, aliphatic ester, halogen or hydroxy group, by an aliphatic hydrocarbon group, or by an aliphatic hydrocarbon group substituted by an alkoxy, cycloalkoxy, aliphatic ester, halogen or hydroxy group, or a salt thereof, but excluding any occurrence of the mixture in vivo.

2. A mixture of an insulin and a 3-hydroxypyrid-4-one in which the carbon atoms of the ring of the 3-hydroxypyrid-4-one each separately are either unsubstituted or substituted by an aliphatic hydrocarbon group, the nitrogen atom being substituted either by an aliphatic hydrocarbon group or by a hydroxy- or alkoxy-substituted aliphatic hydrocarbon group, or a salt thereof, but excluding any occurrence of the mixture in vivo.

3. A mixture according to claim 1, in which the 3-hydroxypyrid-4-one is selected from the group consisting of
3-hydroxy-1,2-dimethylpyrid-4-one,
1-ethyl-3-hydroxy-2-methylpyrid-4-one,
1,2-diethyl-3-hydroxypyrid-4-one,
3-hydroxy-1-(2'-hydroxyethyl)-2-methylpyrid-4-one,
3-hydroxy-1-(2'-hydroxy-1'-methylethyl)-2-methylpyrid-4-one,
3-hydroxy-1-(3'-hydroxypropyl)-2-methylpyrid-4-one,
3-hydroxy-1-(2'-methoxyethyl)-2-methylpyrid-4-one,
3-hydroxy-1-(2'-methoxy-1'-methylethyl)-2-methylpyrid-4-one
3-hydroxy-1-(3'-methoxypropyl)-2-methylpyrid-4-one,
1-(2'-ethoxyethyl)-3-hydroxy-2-methylpyrid-4-one,
1-(2'-ethoxy-1'-methylethyl)-3-hydroxy-2-methylpyrid-4-one,
1-(3'-ethoxypropyl)-3-hydroxy-2-methylpyrid-4-one,
and salts thereof.

4. A mixture according to claim 3, in which the 3-hydroxypyrid-4-one is a 3-hydroxy-1-(2'-methoxyethyl)-2-, methylpyrid-4-one or a salt thereof.

5. A mixture according to claim 1 in which the ratio by weight of the hydroxypyridone: the insulin is in the range of 0.1:1 to 10:1.

6. A pharmaceutical composition which comprises a mixture of an insulin and a 3-hydroxypyrid-4-one in which the hydrogen atom attached to the nitrogen atom is substituted by an aliphatic acyl group, by an aliphatic hydrocarbon group, or by an aliphatic hydrocarbon group substituted by one or more substituents selected from the group consisting of aliphatic acyl, alkoxy, cycloalkoxy, aliphatic amide, aliphatic ester, halogen and hydroxy groups and in which the carbon atoms of the ring of the 3-hydroxypyrid-4-one each separately are either unsubstituted or substituted by an aliphatic acyl, alkoxy, cycloalkoxy, aliphatic amide, aliphatic ester, halogen or hydroxy group, by an aliphatic hydrocarbon group, or by aliphatic hydrocarbon group substituted by an alkoxy, cycloalkoxy, aliphatic ester, halogen or hydroxy group, or a salt thereof, together with a physiologically acceptable diluent or carrier.

7. A pharmaceutical composition which comprises an insulin and a 3-hydroxypyrid-4-one in which the carbon atoms of the ring of the 3-hydroxypyrid-4-one each separately are either unsubstituted or substituted by an aliphatic hydrocarbon group or by a hydroxy- or alkoxy-substituted aliphatic hydrocarbon group, or a salt thereof, together with a physiologically acceptable diluent or carrier.

8. A pharmaceutical composition according to claim 7, in which the 3-hydroxypyrid-4-one is selected from 3-hydroxy-1,2-dimethylpyrid-4-one,
1-ethyl-3-hydroxy-2-methylpyrid-4-one,
1,2-diethyl-3-hydroxypyrid-4-one,
3-hydroxy-1-(2'-hydroxyethyl)-2-methylpyrid-4-one,
3-hydroxy-1-(2'-hydroxy-1'-methylethyl)-2-methylpyrid-4-one,
3-hydroxy-1-(3'-hydroxypropyl)-2-methylpyrid-4-one,
3-hydroxy-1-(2'-methoxyethyl)-2-methylpyrid-4-one,
3-hydroxy-1-(2'-methoxy-1'-methylethyl)-2-methylpyrid-4-one
3-hydroxy-1-(3'-methoxypropyl)-2-methylpyrid-4-one,
1-(2'-ethoxyethyl)-3-hydroxy-2-methylpyrid-4-one,
1-(2'-ethoxy-1'-methylethyl)-3-hydroxy-2-methylpyrid-4-one,
1-(3'-ethoxypropyl)-3-hydroxy-2-methylpyrid-4-one,
and salts thereof.

9. A pharmaceutical composition according to claim 8, in which the 3-hydroxypyrid-4-one is a 3-hydroxy-1-(2'-methoxyethyl)-2-methylpyrid-4-one or a salt thereof.

10. A method of administering insulin to a patient having diabetes mellitus which comprises administering to said patient a therapeutically effective amount of said insulin in admixture with a 3-hydroxypyrid-4-one in which the hydrogen atom attached to the Nitrogen atom is substituted by an aliphatic acyl group, by an aliphatic hydrocarbon group, or by an aliphatic hydrocarbon group substituted by one or more substituents selected from the group consisting of aliphatic acyl, alkoxy, cycloalkoxy, aliphatic amide, aliphatic ester, halogen and hydroxy groups and in which the carbon atoms of the ring of the 3-hydroxypyrid-4-one each separately are either unsubstituted or substituted by an aliphatic acyl, alkoxy, cycloalkoxy, aliphatic amide, aliphatic ester, halogen or hydroxy group, by an aliphatic hydrocarbon group, or by an aliphatic hydrocarbon group substituted by an alkoxy, cycloalkoxy, aliphatic ester, halogen or hydroxy group, or a salt thereof.

11. A method of administering insulin to a patient having diabetes mellitus which comprises administering to said patient a therapeutically effective amount of said insulin in admixture with a 3-hydroxypyrid-4-one in which the carbon atoms of the ring each separately are either unsubstituted or are substituted by an aliphatic hydrocarbon group, the nitrogen atom being substituted either by an aliphatic hydrocarbon group or by a hydroxy- or alkoxy-substituted aliphatic hydrocarbon group, or a salt thereof.

12. A method according to claim 11, in which the 3-hydropyrid-4-one is selected from the group consisting of
3-hydroxy-1,2-dimethylpyrid-4-one,
3-hydroxy-2-,-dimethylpyrid-4-one,
1-ethyl-3-hydroxy-2-methylpyrid-4-one,
1,2-diethyl-3-hydroxypyrid-4-one,
3-hydroxy-1-(2'-hydroxyethyl)-2-methylpyrid-4-one,
3-hydroxy-1-(2'-hydroxy-1'-methylethyl)-2-methylpyrid-4-one,
3-hydroxy-1-(3'-hydroxypropyl)-2-methylpyrid-4-one,
3-hydroxy-1-(2'-methoxyethyl)-2-methylpyrid-4-one,
3-hydroxy-1-(2'-methoxy-1'-methylethyl)-2-methylpyrid-4-one
3-hydroxy-1-(3'-methoxypropyl)-2-methylpyrid-4-one,
1-(2'-ethoxyethyl)-3-hydroxy-2-methylpyrid-4-one,
1-(2'-ethoxy-1'-methylethyl)-3-hydroxy-2-methylpyrid-4-one,
1-(3'-ethoxypropyl)-3-hydroxy-2-methylpyrid-4-one,
and salts thereof.

13. A method according to claim 12, in which the 3-hydroxpyrid-4-one is 3-hydroxy-1-(2'-methoxyethyl)-2-methylpyrid-4-one or a salt thereof.

* * * * *